United States Patent [19]
Dow

[11] Patent Number: 5,457,237
[45] Date of Patent: Oct. 10, 1995

[54] DIHYDROXYINDANONE TYROSINE KINASE INHIBITORS

[75] Inventor: Robert L. Dow, Waterford, Conn.

[73] Assignee: Pfizer Inc., New York, N.Y.

[21] Appl. No.: 142,285

[22] PCT Filed: Apr. 2, 1992

[86] PCT No.: PCT/US92/02444

§ 371 Date: Nov. 23, 1993

§ 102(e) Date: Nov. 23, 1993

Related U.S. Application Data

[63] Continuation of Ser. No. 760,630, May 29, 1991, abandoned.

[51] Int. Cl.$^6$ .......... A61K 31/12; A61K 31/18; C07C 49/747; C07C 311/37
[52] U.S. Cl. .......... 568/327; 514/448; 514/569; 514/603; 514/604; 514/617; 514/618; 514/619; 514/730; 514/824; 549/461; 549/488; 549/498; 562/462; 564/86; 564/87; 564/92; 564/162; 564/166; 564/168
[58] Field of Search .......... 568/327; 514/730, 514/448, 569, 603, 604, 617, 618, 619, 824; 549/461, 488, 498; 562/462; 564/86, 87, 92, 162, 166, 168

[56] References Cited

U.S. PATENT DOCUMENTS 3,932,498  1/1976  Shen et al. .......... 260/515 A
4,535,086  8/1985  Klaus et al. .......... 514/461
5,225,436  7/1993  Shih et al. .......... 514/440

FOREIGN PATENT DOCUMENTS 2091999  8/1982  United Kingdom.
2135999  9/1984  United Kingdom.

OTHER PUBLICATIONS

Drugs of the Future, 11, (1986) pp. 1029–1033.
Arch. Pharmacol 317, (1981) pp. 100–102.
J. Nat. Product 52, No. 6, (1989) pp. 1252–1257.
J. Nat. Products 52, No. 5, (1989) pp. 982–986.
Biochem. Biophys. Res. Comm. 165, No. 1, (1989) pp. 241–245.
Liebigs Annalen der Chemie, 661, (1963) L. Horner et al. pp. 44–52.
Tetrahedron, 39, 17, (1983), F. D. Bellamy et al., pp. 2803–2806.

*Primary Examiner*—Peter O'Sullivan
*Attorney, Agent, or Firm*—Peter C. Richardson; Gregg C. Benson; A. Dean Olson

[57] ABSTRACT

Certain dihydroxyindanone compounds, and their pharmaceutically-acceptable salts, are inhibitors of tyrosine kinase enzymes, and so are useful for the control of tyrosine kinase dependent diseases (e.g., cancer, atherosclerosis).

12 Claims, No Drawings

DIHYDROXYINDANONE TYROSINE KINASE INHIBITORS

This application was filed under 35 U.S.C. §371 based on PCT/US92/02444, which was filed on April 2, 1992 which is a continuation of U.S. application serial no. 07/760,630 which was filed on May 29, 1991 and is now abandoned.

This invention relates to dihydroxyindanone compounds which are tyrosine kinase inhibitors useful for the control of cancer, antiangiogenesis and atherosclerosis.

BACKGROUND OF THE INVENTION

Tyrosine-specific protein kinases (tyrosine kinases) represent a family of enzymes which catalyze the transfer of the terminal phosphate of adenosine triphosphate to tyrosine residues in protein substrates. The first members of this class to be identified were tyrosine kinases associated with viral genes (termed oncogenes) which were capable of cell transformation (i.e. pp60v-src and pp98v-fps). Later it was shown that there were normal cellular counterparts (i.e. pp60c-src and pp98c-fps) to these viral gene products. A third category of tyrosine kinases to be identified are those termed the growth factor receptors, which includes insulin, epidermal growth factor, and p185HER-2 receptors. All of these tyrosine kinases are believed, by way of substrate phosphorylation, to play critical roles in signal transduction for a number of cell functions.

Though the exact mechanisms of signal transduction have yet to be elucidated, tyrosine kinases have been shown to be important contributing factors in cell proliferation, carcinogenesis and cell differentiation. Therefore, inhibitors of these tyrosine kinases are useful for the prevention and chemotherapy of proliferative diseases dependent on these enzymes.

SUMMARY OF THE INVENTION

This invention is directed to dihydroxyindanone compounds that are useful as tyrosine kinase inhibitors. The compounds of this invention have the formula

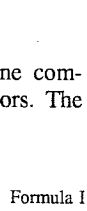

Formula I and pharmaceutically-acceptable salts and prodrugs thereof wherein $R_2$ is halo, COOH, $NO_2$, H,

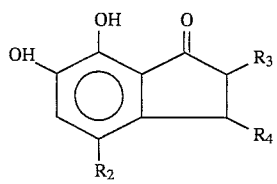

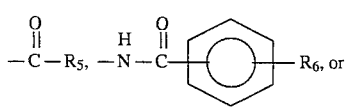

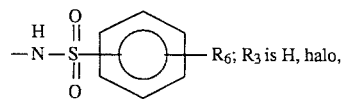; $R_3$ is H, halo,

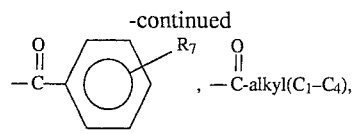

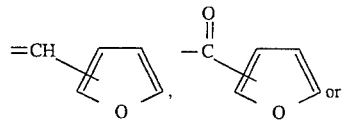

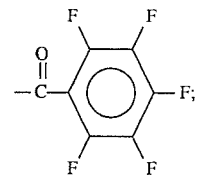

$R_4$ is H, alkyl ($C_1$–$C_6$) or phenyl;

$R_5$ is phenyl, phenylalkyl ($C_1$–$C_3$), —NH-phenyl, hydroxyphenyl, —($C_1$–$C_4$) alkyl or thienyl;

$R_6$ is ($C_1$–$C_6$) alkyl, nitro, perhaloalkyl ($C_1$–$C_4$), halo, —$SO_2$-alkyl ($C_1$–$C_4$)

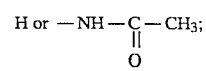

and $R_7$ is H, halo, perhaloalkyl($C_1$–$C_4$), alkoxy($C_1$–$C_3$); with the proviso that at least two of $R_2$, $R_3$ or $R_4$ is H and when $R_3$ and $R_4$ are H, $R_2$ can't be H.

A first group of preferred compounds of Formula I are compounds wherein $R_2$ and $R_4$ are H. Especially preferred within this first preferred group are compounds when $R_3$ is halo,

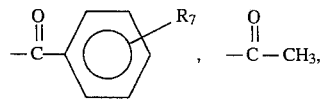

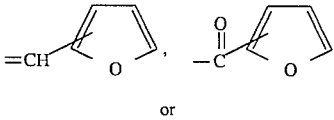

or

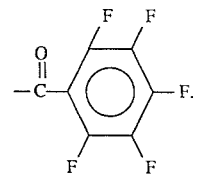

Preferred within this latter group are compounds wherein $R_7$ is H, halo, trifluoromethyl or methoxy.

A second group of preferred compounds of Formula I are those wherein $R_2$ and $R_3$ are H. Especially, preferred within this second preferred group are compounds wherein $R_4$ is phenyl or n-butyl.

A third group of preferred compounds of Formula I are those wherein $R_3$ and $R_4$ are H. A first group of especially preferred compounds within this third preferred group are compounds wherein $R_2$ is halo, $NO_2$, —$CO_2$alkyl($C_1$–$C_4$) or COOH. A second group of especially preferred compounds within this third preferred group of Formula I compounds are compounds wherein $R_2$ is

Preferred within this latter group are compounds wherein $R_5$ is phenyl, phenethyl, —NH-phenyl, hydroxyphenyl, propyl or thiophene. Preferred within this group are compounds wherein $R_5$ is phenyl, phenethyl, —NH-phenyl, 2-hydroxyphenyl, propyl or 3-thiophene. A third group of especially preferred compounds within this third preferred group of Formula I compounds are compounds wherein $R_2$ is

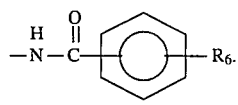

Preferred within this latter group are compounds wherein $R_2$ is

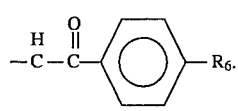

Preferred within this latter group are compounds wherein $R_6$ is t-butyl, nitro, trifluoromethyl, $-SO_2$-methyl or H. A fourth group of especially preferred compounds within this third preferred group of Formula I compounds are compounds wherein $R_2$ is

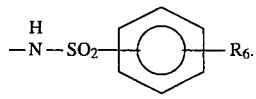

Preferred within this latter group are compounds wherein $R_2$ is

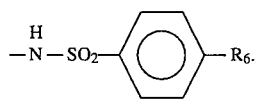

Preferred within this latter group are compounds wherein $R_6$ is t-butyl, nitro, iodo, H or

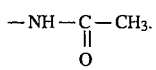

The present invention is also directed to pharmaceutical compositions for the control of tyrosine kinase dependent diseases in mammals which comprise a compound of the formula I in a pharmaceutically-acceptable carrier; and to a method of controlling tyrosine kinase dependent diseases which comprises administering to a mammal suffering from tyrosine kinase dependent diseases a tyrosine kinase dependent disease controlling amount of a compound of the formula I.

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl- 1,3-propanediol).

The expression "prodrug" refers to compounds which are drug precursors which, following administration and absorption, release the drug in vivo via some metabolic process. Exemplary prodrugs are alkyl ethers, acyl esters, and acid esters of the phenolic compounds such as methylether, esters of alkanoic ($C_1$–$C_{10}$)acids, and acids of the formula

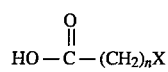

wherein n is 1 to 6 and X is an amino or carboxyl (acid, ester) group, and the formula

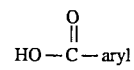

or $-CO_2$alkyl ($C_1$–$C_4$).

Other features and advantages will be apparent from the specification and claims.

DETAILED DESCRIPTION OF THE INVENTION

REACTION SCHEME I

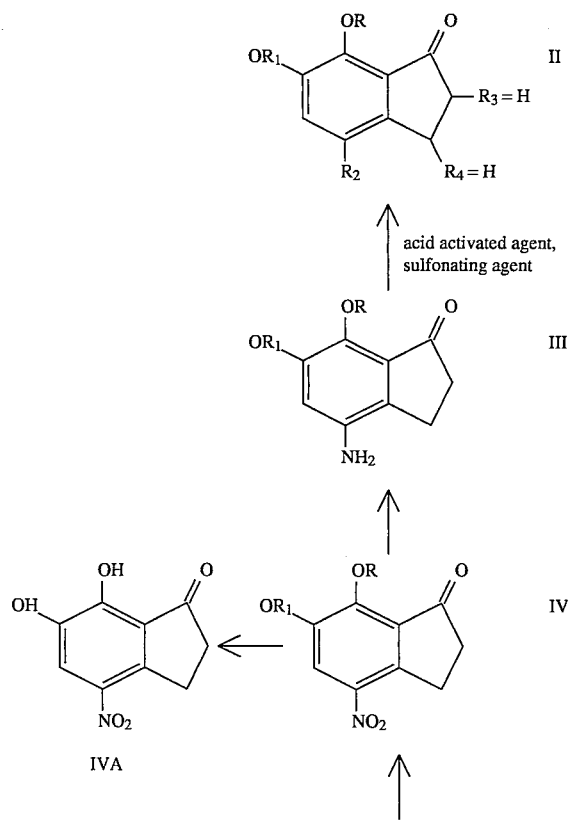

-continued
REACTION SCHEME I
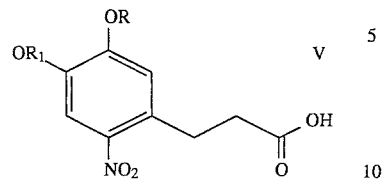
REACTION SCHEME II
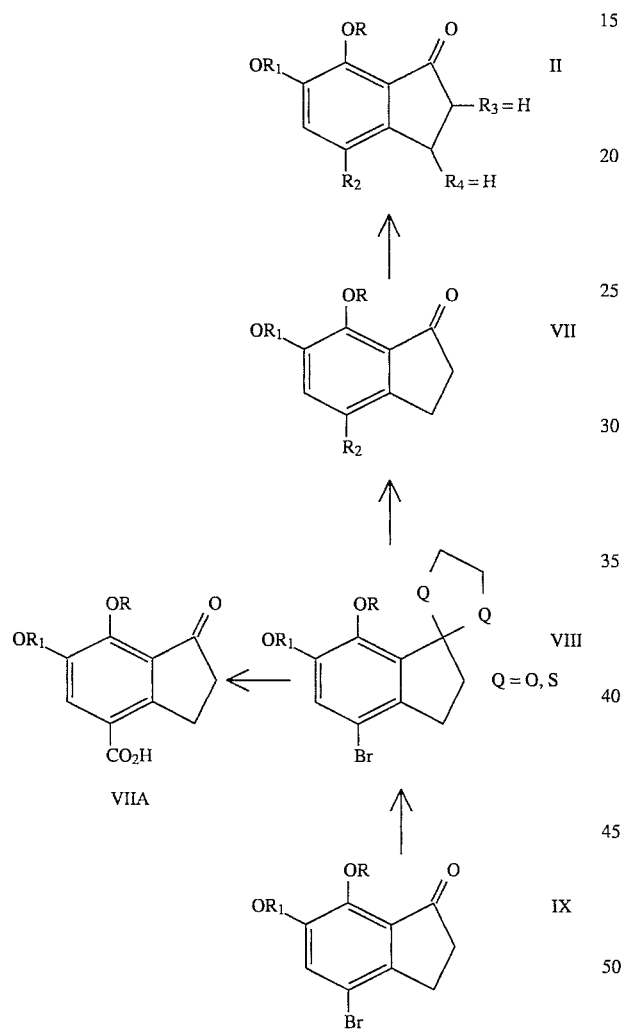

REACTION SCHEME III

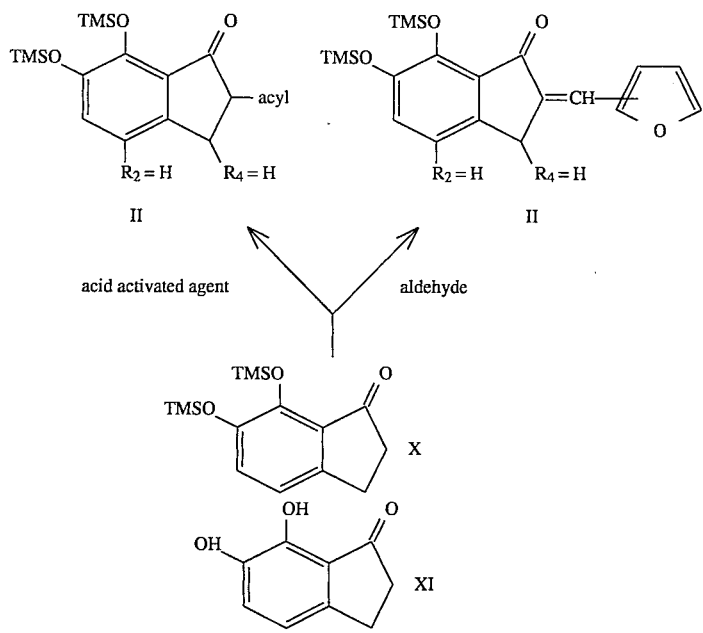

REACTION SCHEME IV

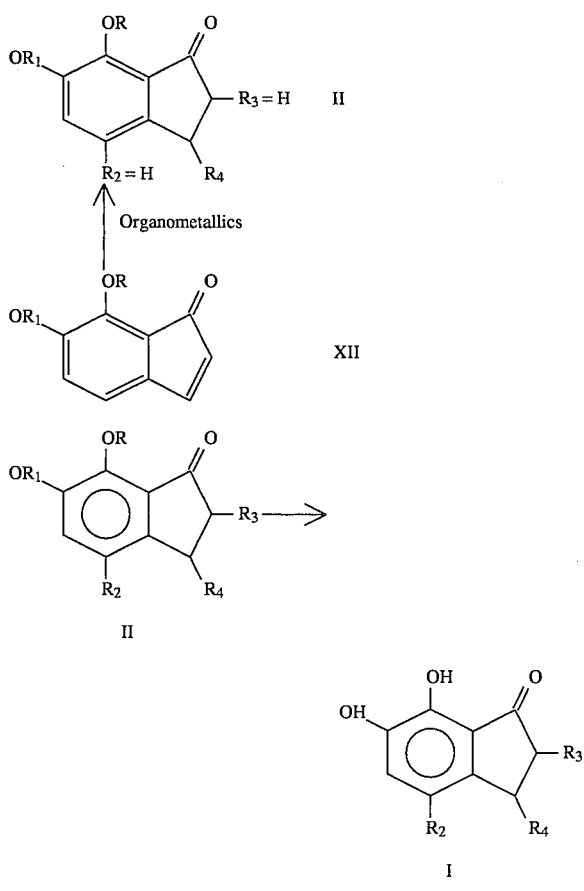

According to the above reaction Formula I compounds wherein $R_2$, $R_3$ and $R_4$ are as defined above may be prepared from Formula II compounds wherein $R_2$, $R_3$ and $R_4$ are as defined above and R and $R_1$ are alkyl($C_1$–$C_4$) or trialkylsilyl by deprotection.

More specifically, when R and $R_1$ are alkyl($C_1$–$C_4$) the Formula II compounds are deprotected by exposure to dealkylating agents such as mineral acids, $BBr_3$, or trialkylsilyl halide at temperatures of 0° C. to 50° C. for 2 to 24 hours. Alternatively, when R and $R_1$ are trialkylsilyl the Formula II compounds are deprotected by exposure to desilylating agents such as dilute acids i.e., HF, HBr, HCl or acetic acid or tetraalkylammonium fluorides such as tetrabutylammonium fluoride at temperatures of 0° C. to 100° C. for 1 to 12 hours.

According to Reaction Scheme I Formula II compounds, wherein R and $R_1$ are alkyl($C_1$–$C_4$), $R_3$ and $R_4$ are H, and $R_2$ is the secondary amides defined above, may be prepared from the appropriate Formula III compounds wherein R and $R_1$ are alkyl($C_1$–$C_4$) by acylation or sulfonation.

The above Formula III compounds are acylated by reaction with the appropriate activated acid agent such as acid halides or anhydrides at temperatures of 0° C. to 50° C. in a solvent such as dichloromethane for 1 to 8 hours. Typically the reaction is run in the presence of a base that is capable of absorbing the counterion such as an alkyl amine or sodium bicarbonate. The Formula III compounds are sulfonated in an analogous manner to that described above using the appropriate sulfonating agent such as a sulfonyl halide.

According to Reaction Scheme I Formula III compounds wherein R and $R_1$ are alkyl($C_1$–$C_4$) may be prepared from the appropriate Formula IV compounds wherein R and $R_1$ are alkyl($C_1$–$C_4$) by reduction.

Generally Formula IV compounds are reduced by exposure to hydrogen in the presence of a noble metal catalyst at pressures of 20 to 50 psi and temperatures of ambient to 100° C. for 2 to 24 hours. Typically the Formula III compounds are prepared in a solvent such as an alcohol or tetrahydrofuran. Alternatively the Formula IV compounds may be reduced with a metal such as zinc or iron at temperatures of ambient to 100° C. at ambient pressure in a protic solvent such as acetic acid for 0.5 to 4 hours.

In addition Formula IVA compounds wherein R and $R_1$ are H may be formed by deprotection of the appropriate Formula IV compounds wherein R and $R_1$ are alkyl($C_1$–$C_4$) using analogous methods to that described above for the deprotection of the Formula ! I compounds to the Formula I compounds.

According to Reaction Scheme I Formula IV compounds wherein R and $R_1$ are alkyl($C_1$–$C_4$) may be prepared from the appropriate Formula V compounds wherein R and $R_1$ are alkyl($C_1$–$C_4$) by cyclization (i.e. Friedel-Crafts). Typically the Formula V compounds are exposed to a Lewis acid catalyst such as $BF_3$, mineral acids, or polyphosphoric acid at temperatures of ambient to 100° C. in the absence of a solvent.

According to Reaction Scheme II Formula II compounds wherein R and $R_1$ are alkyl ($C_1$–$C_4$), $R_3$ and $R_4$ are H, and $R_2$ is

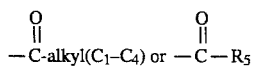

may be prepared from the appropriate Formula VII compounds wherein R and $R_1$ are alkyl($C_1$–$C_4$) and, wherein the carbonyl (within $R_2$) is present in its reduced form (i.e. hydroxy) by oxidation.

Generally, the Formula VII compounds are oxidized by reaction with a pyridine sulfurtrioxide complex in a solvent such as DMSO in the presence of a trialkylamine at a temperature of 0° C. to 50° C. for 30 minutes to 2 hours.

According to Reaction Scheme II Formula VII compounds wherein $R_1$ and R are alkyl($C_1$–$C_4$) and wherein the carbonyl (within $R_2$) is present in its reduced form (i.e. hydroxy) may be prepared from the appropriate Formula VIII compound wherein $R_1$ and R are alkyl($C_1$–$C_4$) by metalation and condensation with the appropriate aldehyde.

Generally the Formula VIII compounds undergo a metal halogen exchange with an aryl or alkyl metal base such as n-butyl lithium or n-phenyl lithium at –78° C. to 0° C. in diethyl ether at ambient pressures for a half hour to two hours. The organometallic compound is then condensed with the appropriate aldehyde at temperatures of –78° C. to 0° C. in the above solvent for 1 hour to 4 hours time.

According to Reaction Scheme II Formula VIIA compounds wherein R and $R_1$ are alkyl($C_1$–$C_4$) and $R_2$ is —COOH may be prepared from Formula VIII compounds wherein R and $R_1$ are alkyl($C_1$–$C_4$) in an analogous manner to the above described conversion of Formula VIII compounds into Formula VII compounds, except that $CO_2$ is used in place of the aldehyde.

According to Reaction Scheme II Formula VIII compounds wherein R and $R_1$ are alkyl($C_1$–$C_4$) may be prepared from the appropriate Formula IX compounds by protection of the carbonyl functionality.

Typically Formula IX compounds are reacted with a carbonyl protecting group (e.g. diols, dithianes) in a non-hydroxyl solvent such as an aromatic or hydrocarbon solvent in the presence of a catalytic acid such as toluene sulfonic acid with the simultaneous removal of water. Generally the reaction is performed at ambient pressure and reflux conditions.

According to Reaction Scheme III Formula II compounds wherein R and $R_1$ are trimethylsilyl (TMSO) and $R_2$ and $R_4$ are H and $R_3$ is

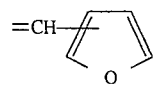

may be prepared from the appropriate Formula X compounds by enolization and aldehyde condensation.

Typically the Formula X compounds are exposed to strong bases such as metal amide bases, (e.g. lithium diisopropyl amide) at temperatures of –78° C. to 0° C. in a non-hydroxylic solvent such as tetrahydrofuran for 0.5 hour to 1 hour time. The resulting compounds are then reacted with the appropriate aldehyde at temperatures –78° C. to 0° C. for 1 to 6 hours.

According to Reaction Scheme III Formula II compounds wherein R and $R_1$ are TMSO, $R_2$ and $R_4$ are H and $R_3$ is acyl as defined above may be prepared from the appropriate Formula X compounds by an analogous procedure to that used above except for the substitution of an acylating agent for the above described aldehyde condensation. Typically the acylation occurs by reaction with the appropriate activated acid agents such as acid halides or anhydrides at temperatures of –78° C. to 0° C. in non-hydroxylic solvent such as tetrahydrofuran for 1 to 6 hours.

According to Reaction Scheme III Formula X compounds may be prepared from the appropriate Formula XI compounds by silylation.

Typically the Formula XI compound is made from the alkoxy precursor using the previously described deprotection conditions. The resulting deprotected Formula XI compounds are then protected by reaction with a silylating agent e.g. hexamethyldisilazane at temperatures of 50° C. to 150° C. in the absence of a solvent for about 2 to about 12 hours.

According to Reaction Scheme IV Formula II compounds wherein R and $R_1$ are alkyl($C_1$–$C_4$), $R_2$ and $R_3$ are H and $R_4$ is as defined above may be prepared from Formula XII compounds wherein R and $R_1$ are alkyl($C_1$–$C_4$) by a catalyzed conjugate addition.

Typically the Formula XII compound is reacted with an alkyl or aryl organometallic such as organolithium reagents or organomagnesium reagents at a temperature of –30° C. to ambient in an ethereal solvent such tetrahydrofuran for 1 to 6 hours. Typically the reaction is catalyzed with a metal halide such as copper (I) iodide.

The starting materials for the above described reaction schemes (e.g. Formula V, IX, XI and XII compounds and the acid activated agents, sulfonating agents, aldehydes, organometallics or amines) can be easily synthesized by those skilled in the art starting from common chemical reagents using conventional methods of organic synthesis.

The compounds of this invention are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The acyl prodrugs of the present phenolic compounds may be prepared by acylation of the bicyclic phenolic compounds with the appropriate acid halide/anhydride in the presence of an organic amine base (e.g. pyridine, $Et_3N$). The ester prodrugs may be prepared from the acids by typical esterification. In addition, prodrugs may be prepared by simply not deprotecting the final compounds.

The compounds of this invention are all readily adapted to therapeutic use as tyrosine kinase inhibitors for the control of tyrosine kinase dependent diseases in mammals. Tyrosine kinase dependent diseases refer to hyperproliferative disorders which are initiated/maintained by aberrant tyrosine kinase enzyme activity. Examples include cancer, atherosclerosis, antiangiogenesis (e.g., tumor growth, diabetic retinopathy), etc.

The in vitro tyrosine kinase inhibitory activity of the present compounds may be demonstrated by methods based on standard procedures. In one method the enzyme pp60src, a tyrosine-specific phosphokinase (tyrosine kinase) associated with the inner surface of the plasma membrane, is purified from Rous sarcoma virustransformed rat cells. In the basis assay the enzyme is incubated with the substrate, val5 angiotensin II, and gamma-32p-ATP in a total volume of 25 µl for 25 minutes at 30° C. according to Wong, T. W., Goldberg, A. R., *J. Biol. Chem.*, 259, 8505–8512 (1984). The reaction is terminated by the addition of 45 µl of 5% TCA, incubated on ice for 5 minutes and centrifuged for 1 minute to remove precipitated protein. 35 µl aliquots of the supernatants are applied to phosphocellular paper circles, which are then washed in 3 changes of 0.5% $H_3PO_4$, acetone-rinsed, dried and counted by liquid scintillation. For screening, the compound to be tested is included in the 25 µl incubation mixture; compounds are tested at 10-4M, 10-5M and 10-6M and appropriate solvent controls are included in all assays.

The compounds are administered either orally or parenterally, or topically as eye drops, in dosages ranging from about 0.1 to 10 mg/kg of body weight per day in single or divided doses. Of course, in particular situations, at the discretion of the attending physician, doses outside of this range will be used.

The compounds of this invention can be administered in a wide variety of different dosage forms, i.e., they may be combined with various pharmaceutically-acceptable inert carriers in the form of tablets, capsules, lozenges, troches, hard candies, powders, sprays, elixirs, syrups, injectable or eye drop solutions, and the like. Such carriers include solid diluents or fillers, sterile aqueous media and various non-toxic organic solvents.

For purposes of oral administration, tablets containing various excipients such as sodium citrate, calcium carbonate and calcium phosphate are employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the essential active ingredient therein can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated. Such aqueous solutions should be suitable buffered, if necessary, and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of topical administration, dilute sterile, aqueous solutions (usually in about 0.1% to 5% concentration), otherwise similar to the above parenteral solutions, are prepared in containers suitable for dropwise administration to the eye.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

It should be understood that the invention is not limited to the particular embodiments shown and described herein, but that various changes and modifications may be made without departing from the spirit and scope of this novel concept as defined by the following claims.

EXAMPLE 1

6,7-Dihydroxyindan-1-one—To a cooled (0° C.), stirred solution of 6,7-dimethoxyindan-1-one (0.2 g, 1.0 mmol) in dichloromethane (5 mL) was added boron tribromide (0.25 mL, 2.60 mmol). After 0.5 hour, the reaction mixture was poured on ice and extracted with EtOAc. The organic layer was washed with brine, dried ($Na_2SO_4$) and concentrated in vacuo. The residue was recrystallized from toluene to afford the title compound (0.8 g); m.p. 141°–143° C. (lit. m.p. 137° C.—Horner, L.; et al. *Liebigs Ann.* 1963, 661, 44).

The following (Examples 2–19) were prepared using the procedure employed in preparation of 6,7-dihydroxyindan-1-one:

4-Bromo-6,7-dimethoxyindan-1-one; m.p. 180°–182° C. (toluene). Anal. Calcd. for $C_9H_7BrO_3$: C, 44.47; H, 2.90. Found: C, 44.76; H, 2.91.

4-Nitro-6,7-dimethoxyindan-1-one; m.p. 202°–204° C. (acetone/EtOAc). Anal. Calcd. for $C_9H_7NO_5.0.25H_2O$: C, 50.62; H, 3.54; N, 6.56. Found: C, 50.88; H, 3.40; N, 6.36.

4-N-(4-Nitrobenzoyl)amino-6,7-dimethoxyindan- 1-one; m.p. >240° C. (acetone/hexanes). Anal. Calcd. for $C_{16}H_{12}N_2O_6.0.75H_2O$: C, 56.2 3; H, 3.98; N, 8.19. Found: C, 56.45; H, 3.52; N, 7.88.

4-N-(4-(Trifluoromethyl)benzoyl)amino-6,7-dimethoxyindan- 1-one; m.p. 175° C. dec (EtOAc/hexanes). Anal. Calcd. for $C_{17}H_{12}F_3NO_4.0.7\ 5H_2O$: C, 55.97; H, 3.73; N, 3.84. Found: C, 55.86 ; H, 3.30; N, 3.93.

4-N-(4-(tert-Butyl)benzoyl) amino-6,7-dimethoxyindan-1-one; m.p. 224°–226° C. (EtOAc/hexanes). Anal. Calcd. for $C_{20}H_{21}NO_4.0.5H_2O$: C, 68.95; H, 6.36; N, 4.02. Found: C, 68.70; H, 6.12; N, 4.07.

4-N-(4-(Sulfonylmethyl)benzoyl)amino-6,7-dimethoxyindan- 1-one; m.p. 157°–159° C. (acetone/hexanes).

4-N-Benzoylamino-6,7-dimethoxyindan-1-one; m.p. 128°–130° C. (EtOAc/hexanes).

4-N-(Phenylsulfonyl)amino-6,7-dimethoxyindan- 1-one; m.p. 242°–244° C. (EtOAc/hexanes).

4-N-((4-Nitrophenyl) sulfonyl) amino-6,7-dimethoxyindan-1 -one; m.p. >250° C. (EtOAc).

4-N-((tert-Butylphenyl)sulfonyl)amino-6,7-dimethoxyindan- 1-one; m.p. 126°–128° C. (EtOAC/hexanes).

4-N-((4-Iodophenyl)sulfonyl)amino-6,7-dimethoxyindan-1-one; m.p. 195°–198° C. (EtOAc/hexanes).

4-( ((4-Acetamido) phenyl) sulfonyl) amino-6,7-dimethoxyindan- 1-one; m.p. >250° C. (acetone/hexanes).

4-Benzoyl-6,7-dimethoxyindan-1-one; m.p. 168°–170° C. (EtOAc/hexanes). Anal. Calcd. for $C_{16}H_{12}O_4 \cdot 0.1H_2O$: C, 71.15; H, 4.56. Found: C, 70.91; H, 4.90.

4-Butanoyl-6,7-dimethoxyindan-1-one; m. p. 115°–117° C. (EtOAc/hexanes).

4-( 3-Phenylpropionoyl ) -6,7-dimethoxyindan-1-one; m.p. 144°–146° C. ($CHCl_3$). Anal. Calcd. for $C_{18}H_{16}O_4 \cdot 0.5H_2O$: C, 70.81; H, 5.45. Found: C, 70.44; H, 5.10.

4-(3-Thienoyl)-6,7-dimethoxyindan-1-one; m.p. 174°–176° C. (EtOAc/hexanes).

4-( 2-Hydroxybenzoyl )-6,7-dimethoxyindan-1-one; m.p. 168°–170° C. (EtOAc/hexanes).

6,7-Dimethoxy-1-oxoindan-4-carboxylic acid; m.p. >240 ° C. (acetone/hexanes).

PREPARATION A

4-Bromo-6,7-dimethoxyindan-1-one; prepared according to the procedure of: S. O. DeSilva, et al. *Can. J. Chem.* 1979, 57, 1598.

PREPARATION B 6,7-Dimethoxyindan-1-one; prepared according to the procedure of: S. O. DeSilva, et al. *Can. J. Chem.* 1979, 57, 1598.

PREPARATION C

4-Nitro-6,7-dimethoxyindan-1-one- To stirred, preheated polyphosphoric acid (60 g) was added 3-(2-nitro-4,5-dimethoxyphenyl)propionic acid (Walker, G. N., *J. Amer. Chem. Soc.* 1956, 78, 3698, 3.0 g, 12 mmol). After 2 hours, the reaction mixture was poured over ice and extracted with EtOAc. The organic layer was washed with water, 1N sodium hydroxide, brine, dried ($Na_2SO_4$) and concentrated in vacuo. Flash chromatography of the residue afforded the title compound; m.p. 132°–134° C. Anal. Calcd. for $C_{11}H_{11}NO_5$: C, 55.70; H, 4.67; N, 5.90. Found: C, 55.72; H, 4.59; N, 5.75.

PREPARATION D

4-Amino-6,7-dimethoxyindan-1-one—A mixture of 4-nitro-6,7-dimethoxyindan-1-one (1.0 g, 4.2 mmol) and 10% palladium-on-carbon (0.3 g) was hydrogenated (50 psi) on a Parr apparatus for 5 hours. The reaction mixture was filtered through Celite, filtrate concentrated in vacuo and the residue was recrystallized from EtOAc to afford the title compound; m.p. 178° C. Anal. Calcd. for $C_{11}H_{13}NO_3$: C, 63.75; H, 6.32; N, 6.76. Found: C, 63.20; H, 6.12; N, 6.83.

PREPARATION E

4-N-(4-Nitrobenzoyl)amino-6,7-dimethoxyindan-1-one (0.6 g, 2.9 mmol) and triethylamine (0.6 mL, 4.3 mmol) in dichloromethane (40 mL) was added a solution of 4-nitrobenzoyl chloride (0.6 g, 3.7 mmol). After 0.5 hour, the reaction mixture was poured into 1N sodium hydroxide and extracted with EtOAc. The organic layer was washed with brine, dried ($Na_2SO_4$) and concentrated in vacuo. The resulting solids were recrystallized from acetone to afford the title compound (0.5 g); m.p. 220°–222° C. Anal Calcd for $C_{18}H_{16}N_2O_6 \cdot 0.5H_2O$: C, 59.17; H, 4.69; N, 7.67. Found: C, 59.29; H, 4.50; N, 7.57.

The following compounds (Preparations F-N) were prepared using the above procedure:

4-N-(4-(Trifluoromethyl))benzoyl)amino-6,7-dimethoxyindan- 1-one; m.p. 226°–228° C. (acetone).

4-N-(4-(tert-Butyl)benzoyl)amino-6,7-dimethoxyindan-1-one; m.p. 226° C. (EtOAc) .

4-N-(4-(Sulfonylmethyl)benzoyl)amino-6,7-dimethoxyindan- 1-one; m. p. 202°–203° C.

4-N-Benzoylamino-6,7-dimethoxyindan-1-one; m.p. 158°–159° C. (EtOAc/hexanes).

4-N-(phenylsulfonyl)amino-6,7-dimethoxyindan- 1-one; m.p. 184°–185° C. (MeOH).

4-N-((4-Nitrophenyl)sulfonyl)amino-6,7-dimethoxyindan-1-one; m.p. 140°–143° C. (EtOAc).

4-N-((tert-Butylphenyl)sulfonyl)amino-6,7-dimethoxyindan- 1-one; m.p. 209°–211° C. (EtOAc). Anal. Calcd. for $C_{21}H_{25}NO_5S$: C, 62.51; H, 6.25; N, 3.47. Found: C, 62.22; H, 6.17; N, 2.31.

4-N-((4-Iodophenyl)sulfonyl)amino-6,7-dimethoxyindan-1-one; m.p. 207°–209° C.

4-N-(((4-Acetamido)phenyl)sulfonyl)amino-6,7-dimethoxyindan- 1-one; m.p. >250° C. (THF/hexanes).

PREPARATION O

4-Benzoyl-6,7-dimethoxyindan-1-one - A mixture of 4-bromo-6,7-dimethoxyindan-1-one (0.5 g, 1.8 mmol), ethylene glycol (2 mL) and p-toluenesulfonic acid (10 mg) in toluene (40 mL) were refluxed with removal of water (Dean-Stark trap) for 10 hours. The reaction solution was diluted into EtOAc, washed with 10% aqueous sodium bicarbonate, water, dried ($Na_2SO_4$) and concentrated in vacuo to afford the ethylene ketal as a light brown colored solid (0.6 g); m.p. 100°–104° C. A solution of this ketal (1.5 g, 4.7 mmol) in THF (10 mL) was added dropwise to a stirred, cooled (−78° C.) solution of n-butyllithium (2.5M in hexanes, 2.1 mL, 5.2 mmol) in THF (20 mL). After 0.5 hour, benzaldehyde (1.0 mL, 9.4 mmol) was added in one portion. After an additional 1 hour at −78° C., the reaction solution was poured into brine and extracted with EtOAc. The organic phase was washed with brine, dried ($Na_2SO_4$), concentrated in vacuo and the residue was flash chromatographed (50% EtOAc/hexanes) to afford the carbinol (1.3 g) corresponding to the title ketone. To a solution of this carbinol (1.2 g, 3.5 mmol) and triethylamine (4.9 mL, 35 mmol) in DMSO (60 mL) was added pyridine sulfurtrioxide complex (1.7 g, 11 mmol). After 1 hour, the reaction solution was poured into 10% aqueous sodium hydrogen sulfate and extracted with EtOAc. The organic phase was concentrated in vacuo and was dissolved in 1:1 THF:6N HCl and the reaction solution was stirred for 0.5 hour. The reaction mixture was poured into brine and extracted with EtOAc. The organic phase was washed with brine, dried ($Na_2SO_4$) and concentrated in vacuo. The residue was flash chromatographed (50% EtOAc/hexanes) to afford the title compound (0.8 g); m.p. 117°–119° C. (EtOAc/hexanes).

The following compounds (Preparation P-S) were prepared using the above procedure:

4-Butanoyl-6,7-dimethoxyindan-1-one; m.p. 85°–87° C.

4-(3-Phenylpropionoyl)-6,7-dimethoxyindan-1-one; oil.

4-(3-Thienoyl)-6,7-dimethoxyindan-1-one; oil.

4-(2-Methoxybenzoyl)-6,7-dimethoxyindan-1-one; m.p. 96°–98° C. (ether). Anal. Calcd. for $C_{19}H_{18}OS$: C, 69.93; H, 5.56. Found: C, 70.02; H, 5.23.

PREPARATION T 6,7-Dimethoxy-1-oxoindan-4-carboxylic acid—To a stirred, cooled (−78° C.) solution of n-butyllithium (2.5M in hexanes, 0.5 mL, 1.3 mmol) in THF (2 mL) was added a solution of the ethylene ketal of 4-bromo-6,7-dimethoxyindan-1-one (0.35 g, 1.11 mmol—see above procedure for preparation) in THF (4 mL) over a 10 minute period. After an additional 45 minutes, the reaction solution was poured over solid carbon dioxide (20 g) and allowed to stand for 1 hour. The reaction mixture was diluted with ether and extracted twice with water. The combined aqueous phases were acidified with 6 N HCl and extracted with EtOAc. The combined organic phases were dried ($Na_2SO_4$), concentrated in vacuo and the resulting solids were recrystallized from EtOAc/hexanes to afford the title compound (0.15 g); m.p. >230° C. Anal. Calcd. for $C_{12}H_{12}O_5$: C, 61.01; H, 5.12. Found: C, 60.96; H, 5.19.

PREPARATION U 6,7-Di-(trimethylsiloxy)indan-1-one—A mixture of 6,7-dihydroxyindan-1-one (0.3 g, 1.8 mmol), hexamethyldisilazane (4 mL) and concentrated sulfuric acid (1 drop) were heated at 125° C. for 2 hours. The reaction solution was concentrated in vacuo to afford a dark oil, which was taken on to the next step without further purification.

PREPARATION V

2-Benzoyl-6,7-dihydroxyindan-1-one—To a stirred, cooled (−78° C.) solution of diisopropylamine (0.6 mL, 4.2 mmol) in THF (5 mL) was added a 2.5M solution of n-butyllithium (1.7 ml, 4.2 mmol) in hexanes. After 15 minutes, a solution of the disilyl derivative (prepared above) in THF (4 mL) was added over a 5 minute period and the reaction solution was mainted at −78° C. for 45 minutes. Benzoyl chloride (0.2 mL, 2.0 mmol) was added and after 15 minutes the reaction solution was poured into 1N HCl. This mixture was extracted with EtOAc, the organic layer concentrated in vacuo and the resulting oil was dissolved in THF (5 mL)/water (1 mL)/48% aqueous hydrofluoric acid (0.2 mL). After 20 minutes, the reaction solution was taken up in EtOAc, washed with brine, dried ($Na_2SO_4$) and concentrated in vacuo. The residue was flash chromatographed (25% acetone/hexanes) to afford the title compound (0.3 g overall); m.p. 144°–146° C. Anal. Calcd. for $C_{16}H_{12}O_4$: C, 71.63; H, 4.51. Found: C, 71.68; H, 4.52.

The following compounds (Preparations W–Z and AA and AB) were prepared using the above procedure.
2-(3-Bromobenzoyl)-6,7-dihydroxyindan-1-one; m.p. 176°–178° C. Anal. Calcd. for $C_{16}H_{11}BrO_4$: C, 55.36; H, 3.19. Found: C, 55.26; H, 3.23.
2-((4-Trifluoromethyl)benzoyl)-6,7-dihydroxyindan-1-one; m.p. 188°–190° C. (MeOH). Anal. Calcd. for $C_{17}H_{11}F_3O_4$: C, 60.72; H, 3.30. Found: C, 60.34; H, 3.33.
2-(4-Methoxybenzoyl)-6,7-dihydroxyindan-1-one; m.p. 191°–193° C. (MeOH). Anal. Calcd. for $C_{17}H_{14}O_5$: C, 68.45; H, 4.73. Found: C, 68.03; H, 4.73.
2-((2,3,4,5,6-Pentafluoro)benzoyl)-6,7-dihydroxyindan-1-one; m.p. 114°–115° C. (MeOH/H20). Anal. Calcd. for $C_{16}H_7F_5O_4 \cdot 1H_2O$: C, 50.41; H, 2.37. Found: C, 50.41; H, 1.96.
2-Acetyl-6,7-dihydroxyindan-1-one; m.p. 159°–160° C. ($CHCl_3$). Anal. Calcd. for $C_{11}H_{10}O_4$: C, 64.07; H, 4.90. Found: C, 63.38; H, 4.83.
2-(2-Furanoyl)-6,7-dihydroxyindan-1-one; m.p. 184.5°–185° C. ($CHCl_3$/hexanes). Anal. Calcd. for $C_{14}H_{10}O_5$: C, 65.11; H, 3.91. Found: C, 64.75; H, 3.56.

PREPARATION AC 2-((2-Furanyl)methylene)-6,7-dihydroxyindan-1-one—To a stirred, cooled (−78° C.) solution of diisopropylamine (0.3 mL, 2.1 mmol) in THF (4 mL) was added a 2.5M solution of n-butyllithium in hexanes (0.8 mL, 2.0 mmol). After 15 minutes, a solution of 6,7-di (trimethylsiloxy)indan-1-one (0.47 g, 1.52 mmol) in THF (4 mL) over a 5 minute period. After an additional 45 minutes, 2-furaldehyde (0.25 mL, 3.04 mmol) was added; after 15 minutes the reaction solution was poured into 1N HCl and extracted with EtOAc. The organic layer was concentrated in vacuo and stirred in a mixture of THF (5 mL)/$H_2O$ (1 mL)/48% aqueous hydrofluoric acid (0.2 mL) for 0.5 hour. The reaction solution was diluted into EtOAc, washed with brine, dried ($Na_2SO_4$) and concentrated in vacuo. The residue was flash chromatographed (30% acetone/hexanes) to afford the title compound as a yellow solid (35 mg); m.p. 177°–179° C.

PREPARATION AD

2-Bromo-6,7-dihydroxyindan-1-one—Prepared according to the procedure of: Bellamy, F. D.; et al. *Tetrahedron*, 1983, 39, 2803.

PREPARATION AE

3-Phenyl-6,7-dimethoxyindan-1-one—To a stirred, cooled (0° C.) solution of copper (I) iodide (0.4 g, 2.1 mmol) and 1.7M solution of phenyllithium (2.5 mL, 4.2 mmol) in diethyl ether (20 mL) was added dropwise a solution of 6,7-dimethoxy-1H-inden-1-one (0.4 g, 2.1 mmol—Bellamy, F. D.; et al. Tetrahedron 1983, 39, 2803) in THF (30 mL) over a 5 minute period. After 1 hour, the reaction solution was poured into 1N HCl and extracted with EtOAc. The organic layer was washed with brine, dried ($Na_2SO_4$) and concentrated in vacuo. The residue was flash chromtographed (50% EtOAc/hexanes) to afford the title compound (0.3 g) as an oil.

The following compound (Preparation AF) was prepared using the above procedure:
3-n-Butyl-6,7-dimethoxyindan-1-one; m.p. 104°–105° C.

I claim:
1. A compound of the formula

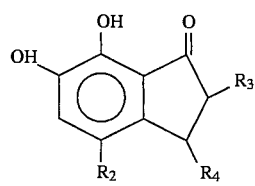

Formula I and pharmaceutically-acceptable salts and prodrugs thereof wherein $R_2$ is halo, COOH, $NO_2$, H,

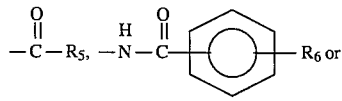

-continued

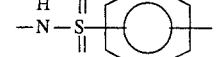

$R_3$ is H, fluoro, chloro, iodo, 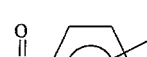,

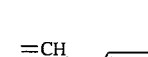

$R_4$ is H, alkyl($C_1$–$C_6$) or phenyl;
$R_5$ is phenyl, phenylalkyl ($C_1$–$C_3$), —NH-phenyl, hydroxphenyl, —($C_1$–$C_4$) alkyl or thienyl;
$R_6$ is ($C_1$–$C_6$)alkyl, nitro, perhaloalkyl($C_1$–$C_4$), halo, —$SO_2$-alkyl($C_1$–$C_4$), H or $$-NH-\underset{\underset{O}{\|}}{C}-CH_3;$$

and
$R_7$ is H, halo, perhaloalkyl ($C_1$–$C_4$), alkoxy($C_1$–$C_3$); with the proviso that at least two of $R_2$, $R_3$ or $R_4$ is H and when $R_3$ and $R_4$ are H, $R_2$ can't be H or Br.

2. A compound of claim 1 wherein $R_2$ and $R_2$ and $R_4$ are H.

3. A compound of claim 2 wherein $R_3$ is fluoro, chloro, iodo,

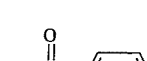

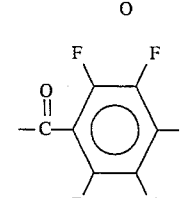

4. A compound of claim 3 wherein $R_7$ is H, halo, trifluoromethyl or methoxy.

5. A compound of claim 4 wherein $R_7$ is in position 3 or 4.

6. A compound of claim 1 wherein $R_2$ and $R_3$ are H.

7. A compound of claim 6 wherein $R_4$ is phenyl or n-butyl.

8. A compound of claim 1 wherein $R_3$ and $R_4$ are H.

9. A compound of claim 8 wherein $R_2$ is halo, $NO_2$, —$CO_2$alkyl($C_1$–$C_4$) or COOH.

10. A compound of claim 8 wherein $R_2$ is $$-\underset{\underset{}{\overset{O}{\|}}}{C}-R_5.$$

11. A compound of claim 10 wherein $R_5$ is phenyl, phenethyl, —NH-phenyl, hydroxyphenyl, propyl or thiophene.

12. A compound of claim 11 wherein $R_5$ is phenyl, phenethyl, —NH-phenyl, 2-hydroxyphenyl, propyl or 3-thiophene.

* * * * *